(12) United States Patent
Esser et al.

(10) Patent No.: US 7,823,745 B2
(45) Date of Patent: Nov. 2, 2010

(54) TUBE, CAP AND RACK FOR AUTOMATIC HANDLING OF SAMPLES

(75) Inventors: Peter Esser, Kobenhavn S (DK); Phil Smith, Cambridge (GB)

(73) Assignee: The Automation Partnership (Cambridge) Limited, Royston, Herfordshire (GB)

( * ) Notice: Subject to any disclaimer, the term of this patent is extended or adjusted under 35 U.S.C. 154(b) by 844 days.

(21) Appl. No.: 11/569,191

(22) PCT Filed: May 18, 2005

(86) PCT No.: PCT/DK2005/000332

§ 371 (c)(1),
(2), (4) Date: Apr. 19, 2007

(87) PCT Pub. No.: WO2005/110600

PCT Pub. Date: Nov. 24, 2005

(65) Prior Publication Data

US 2008/0035642 A1 Feb. 14, 2008

(30) Foreign Application Priority Data

May 18, 2004 (DK) .......................... PA 2004 00788

(51) Int. Cl.
*B65D 90/02* (2006.01)

(52) U.S. Cl. .................................................. 220/669

(58) Field of Classification Search .............. 220/23.89, 220/23.88, 23.87, 23.83, 507, 304, 288, DIG. 7, 220/804, 801, 806, 796, 669, 628, 623, 634, 220/555, 553, 530, 529, 672, 673, 671, 670, 220/600, 660, 200; 215/356, 355, 302, 296, 215/295, 383, 382, DIG. 3, 379, 200; D9/711, D9/439, 443, 452, 435, 455, 759, 756, 751, D9/737, 541, 546, 538, 569, 434, 516
See application file for complete search history.

(56) References Cited

U.S. PATENT DOCUMENTS 52,269 A * 1/1866 Connelly ..................... 215/356
339,556 A * 4/1886 Johnston ..................... 215/296

(Continued)

FOREIGN PATENT DOCUMENTS

DE 4421220 C1 11/1995

(Continued)

*Primary Examiner*—Anthony Stashick
*Assistant Examiner*—Robert J Hicks (57) ABSTRACT

A tube comprising a container having a closed bottom end, an open top end, and a part that is adapted for flexible cooperation with a compartment of a rack for accommodation of the tube in such a way that unintentional removal of the tube from the respective compartment is substantially prevented, a cap for sealing a tube, and a rack for accommodating a plurality of tubes. The tube, cap, and rack facilitate automatic handling of samples.

46 Claims, 8 Drawing Sheets

U.S. PATENT DOCUMENTS

| | | | |
|---|---|---|---|
| 3,747,751 A * | 7/1973 | Miller et al. | 206/277 |
| 4,310,488 A | 1/1982 | Rahm et al. | |
| 4,550,846 A * | 11/1985 | Phillips | 215/296 |
| 5,167,929 A | 12/1992 | Korf et al. | |
| 5,225,165 A * | 7/1993 | Perlman | 422/102 |
| 5,325,980 A * | 7/1994 | Grimm et al. | 220/212 |
| 5,803,285 A * | 9/1998 | Hirota | 215/296 |
| 5,894,733 A | 4/1999 | Brodner | |
| 6,270,728 B1 | 8/2001 | Wijnschenk et al. | |
| 2001/0013169 A1 | 8/2001 | Fassbind et al. | |
| 2004/0033168 A1 * | 2/2004 | Hughes et al. | 422/100 |

FOREIGN PATENT DOCUMENTS

| | | |
|---|---|---|
| EP | 0411274 A2 | 2/1991 |
| EP | 1452869 A | 9/2004 |
| NL | 1018898 C | 3/2003 |
| WO | WO 0147640 A | 7/2001 |

* cited by examiner

TUBE, CAP AND RACK FOR AUTOMATIC HANDLING OF SAMPLES

FIELD OF THE INVENTION

The present invention relates to tubes, tube caps, and tube racks or holders, in particular for use in automatic, e.g. robotic, test systems.

BACKGROUND OF THE INVENTION

In automatic test systems, there is a need for automatic and safe handling of test samples. In recent years there has been an increasing activity within the biotech area and as a consequence thereof an increased need for safe and secure handling, storing and labeling of samples have arisen. The increasing activity has caused a large growth in the number of samples to be tested leading to a demand for tubes, caps and racks, that can be handled automatically during substantially the entire testing, storing, and handling process to provide the above-mentioned automatic and safe handling of test samples.

Furthermore the large number of test samples has created a need for a tube, rack, and cap that take up as little volume as possible either alone or in combination with one of the others.

U.S. Pat. No. 6,270,728 discloses a tube with an optically readable code. The tube has a supporting collar for supporting the tube in the rack. A locking slide is disclosed for fixing the tube in the rack.

SUMMARY OF THE INVENTION

It is an object of the present invention to provide improved tubes, caps, and racks facilitating automatic handling of samples.

According to the invention, a tube comprising a container having a closed bottom end, and an open top end fulfills the above-mentioned and other objects. Further, the tube has a part that is adapted for interaction, e.g. by flexible cooperation, with a rack having compartments with sidewalls for accommodation of the tube in such a way that unintentional removal of the tube from the respective compartment is substantially prevented. The tube and/or the rack may be flexible to provide the flexible cooperation between the two.

The tube may, in a first longitudinal position in one of the rack compartments, be substantially free to rotate about a longitudinal axis of the tube in the compartment while unintentional removal of the tube from the compartment is substantially prevented.

The tube may have an outer circumference of a cross-section in a plane perpendicular to the longitudinal extension of the tube that is non-circular for definition of at least one angular position of the tube that allows movement of the tube into a second longitudinal position in the compartment in which second longitudinal position the tube cannot be rotated.

The part adapted for interaction with the rack may comprise one or more protrusions, e.g. for flexible cooperation with the rack. One or more pins may constitute the protrusions. In a preferred embodiment, the one or more protrusions of the part adapted for interaction with the rack comprise a bead or a ridge, e.g. an O-shaped bead, on the outer surface of the tube for flexible cooperation with the rack. The bead may cover the entire circumference of the tube, or the bead may cover substantially the circumference of the tube, or, it may be divided into sections.

Preferably, during insertion of the tube in a compartment of the rack, the one or more protrusions are forced inside the compartment, whereby the tube and the one or more protrusions are slightly deformed creating a slight resistance against the insertion. When the one or more protrusions reach the open bottom end of the compartment, i.e. has passed or partly passed the sidewalls, the tube is allowed to return to its original shape so that the width of the tube at the one or more protrusions becomes slightly larger than the corresponding width of the compartment so that removal of the tube cannot be performed without application of a force to deform the tube sufficiently to allow the one or more protrusions to re-enter the compartment. Also, the one or more protrusions prevent the tubes from falling out of the compartments if the rack is turned upside down.

Alternatively the compartment or a part thereof is slightly deformed during insertion of the tube in a compartment of the rack creating a slight resistance against the insertion. When the one or more protrusions of the tube reach the open bottom end of the compartment, i.e. has passed or partly passed the sidewalls, the compartment is allowed to return to its original shape so that the width of the tube at the one or more protrusions becomes slightly larger than the corresponding width of the compartment so that removal of the tube cannot be performed without application of a force to deform the compartment sufficiently to allow the one or more protrusions to re-enter the compartment. A combination of temporary deformations of the tube and compartment is also possible.

Advantageously the bead covers the entire circumference of the tube to provide for a more secure and rotationally independent fixing of the tube in the compartments of the rack.

It is an advantage of the invention that during handling of the tube, the tube does not have to be rotationally fitted in order to place the tube in a position in a compartment of the rack. In this position, unintentional removal of the tube from the rack may be prevented. Thus, it may be possible to insert the tube in a compartment of the rack whereby unintentional removal may be prevented, independent of the rotational position around its longitudinal axis.

The one or more protrusions, such as the bead, pin, etc., are preferably located on a part of the tube above the solid bottom of the tube, i.e. on a hollow part of the tube, for increased flexibility.

In an alternative embodiment, one or more protrusions may be provided internally in the compartments for cooperation with corresponding recesses in the one or more parts of the tubes adapted for interaction with the rack for substantially prevention of unintentional removal of the tube from the respective compartment.

Preferably, an outer circumference of a cross-section in a plane perpendicular to the longitudinal extension of the tube and just above the part adapted for interaction with the rack for preventing unintentional removal of the tube from the rack is substantially circular. Due to the substantially circular outer circumference, the tube may rotate substantially freely in one longitudinal position in a compartment.

The tube may be designed so that in at least one position in a compartment of the rack, rotation of the tube is prevented, for example by provision of one or more protrusions on the outer side of the tube, whereby an outer circumference of a cross-section in a plane perpendicular to the longitudinal extension of the tube becomes non-circular. Alternatively or in combination herewith a part of the outer side of the tube may have a cross-section in a plane perpendicular to the longitudinal extension of the tube that is substantially a polygon, e.g. with 3, 5, 6, 7, 8, and preferably 4 sides, an ellipsoid or another noncircular geometrical shape that, in cooperation with a compartment of the rack, prevents rotation of the tube. This facilitates automatic, e.g. rotational, capping and de-capping of the tube.

The inside of the tube may be formed to enhance complete emptying of tube. Providing a tube with no inner sharp edges facilitates this. The bottom of the inside of the tube may be designed, e.g. rounded, to facilitate complete emptying of tube.

The inside surface of the tube may be coated with e.g. an anti-coagulating agent.

The tube is preferably made of a suitable polymer, such as polypropylene, polyethylene, or a combination thereof. Types of polypropylene or polyethylene suitable for tubes are generally known from the prior art. A part of the tube, preferably the bottom, may be colored, preferably in black, to render possible the application of an identification code.

At the closed bottom end of the tube an identification code may be applied to enable identification of the tube and its contents. The code may be written or burned into the tube with a laser, but other methods for labeling the tube, such as gluing an identification piece or foil on the tube, and/or RFID-labeling of the tubes may be employed.

The identification code is preferably a Data Matrix 2D-code with 12×12 or 14×14 dots. Other Data Matrix formats such as 16×16, 18×18, 20×20, or 22×22 or other suitable identification codes may be employed.

Further, a cap may be provided for attachment to the tube whereby the tube is sealed.

The tube may have a threading internally or externally at the open top end part of the tube for cooperation with a threaded cap for attachment, e.g. sealing attachment, of the cap to the tube.

Alternatively or in combination with the threading the tube may internally or externally on the open top end part of the tube comprise one or more protrusions or recesses to provide means for removably fixing a cap in the tube, e.g. in a bayonet clutch.

The cap may have a plug part and a head part, the head part having a part adapted for interaction with a tool for capping or de-capping the tube. The part adapted for interaction with a tool is preferably substantially polygonal but may have any form suitable for engagement with a tool.

In a preferred embodiment the part adapted for interaction with a tool may be a substantially polygonal depression for interaction with a tool for capping or de-capping the tube, whereby the tool functions as the male part and the head part functions as the female part. The depression is preferably substantially square and/or may be substantially polygonal with e.g. 3, 4, 5, 6, 7, 8, or more edges, or another noncircular form suitable for interaction with a tool for rotational coupling of the cap and the tube.

When the cap interacts with the tool for capping and de-capping there is a need for the cap to be removably positioned on the tool. Thus the depression may have at least one recess in a side thereof.

In an embodiment the depression in the head part of the cap may have at least one hole in a side thereof to facilitate removable positioning of the cap on the tool.

In another embodiment the head part may function as male and have a substantially polygonal protrusion for interaction with a female tool for capping or de-capping the tube.

The force to be used for separating the cap and the tool for capping and de-capping the tube is smaller than the force to be used for removing the tube from the rack. Hereby is ensured that the tool for capping or de-capping can be removed from the cap when the tube with the cap is placed in the rack When the tube with the cap is placed in the rack there is a need for removing the tube with the cap from the rack and placing it in e.g. a freezer for cold storage. For enabling a tool to grab and move the tube from the rack the head part may be provided with one or more recesses on the outside surface of the head part for engagement with a tool for positioning of the tube in a compartment of the rack. The at least one recess is preferably annular but may have any other suitable form to enable a tool to, while the tube with the cap is positioned in a compartment of the rack, grab the cap and remove the tube with the cap from the rack.

In another embodiment the tool for grabbing and moving the tube from the rack may engage with a depression in the head part of the cap. In this embodiment the depression for interacting with the tool for grabbing and moving the tube is preferably the same as a depression for interacting with the tool for capping and de-capping.

The cap may further comprise a gasket for completely sealing the tube when the cap is put on or positioned in the tube. In one embodiment the gasket is an O-ring or a flat gasket. In another embodiment the gasket is molded on the cap during manufacturing, whereby the gasket becomes an integrated part of the cap. The gasket is preferably made of silicone rubber, but other suitable materials such as a polypropylene or polyethylene based elastomer are also useful.

Further the cap may comprise a threading on the plug part for engagement with the tube to provide a secure attachment of the cap to the tube.

In another embodiment the plug may instead of or in combination with a threading comprise one or more protrusions or recesses to provide means for removably fixing the cap in the tube, e.g. in a bayonet clutch.

To facilitate easy engagement of the cap with the tube in the automatic test system the end of the plug part may be tapered/chamfered.

The head part of the cap may further comprise one or a plurality of longitudinal recesses on the outer surface of the head part to facilitate manual capping and de-capping.

The cap is preferably made of polypropylene, but other materials such as polyethylene, silicone rubber, polypropylene or polyethylene based elastomers, or a combination may be used.

A tool is provided for capping and de-capping the tube and a tool is provided for moving the tube with the cap from the rack. The tool for moving the tube with the cap from the rack may be integrated in the tool for capping and de-capping the tube. A tool for handling a plurality of tubes is conceived.

Further, in accordance with the invention a rack may be provided for holding a plurality of the tubes of the present invention. The rack comprises a frame with a plurality of compartments for holding a plurality of tubes according to the present invention, the plurality of compartments adapted for interaction with the tube part adapted for interaction with the rack whereby unintentional removal of the tube from the respective compartment is substantially prevented.

The compartments have an open top end and an open bottom end. Therefore the bottom of the tubes when tubes are placed in the rack is visible from the underside of the rack. Thus, when tubes are placed in at least one of the compartments of the rack, possibly all, it is possible to optically scan the bottom of the tubes to e.g. read a code from the tubes to provide for identification of the tubes and their content.

Preferably, the rack comprises 96 compartments in an 8×12 matrix formation, but other formations, such as 384 compartments in a 16×24 matrix formation are also possible.

Preferably, the compartments are quadratic having four sidewalls, but may be of any non-circular shape. A compartment has a non-circular shape when a cross-section of the compartment at a certain depth is non-circular. The non-circular shape of the compartments assists in preventing a tube from rotating in at least one position of the tube in the compartment. The center-to-center distance between adjacent compartments is a standard distance between 8 and 10 mm, preferably 9 mm. To facilitate use of standard apparatus for automatic systems, e.g. conveyor belts, the rack may comply with some of the standard dimensions of the SBS (Society of Biomolecular Screening)-standard, e.g. the length and width of the footprint of the rack, placement of compartments in rack, and the center-to-center distance between wells/compartments.

In a preferred embodiment of the rack the sidewalls of the compartments are slightly oblique whereby the cross-section at the open top end of the compartment is larger than the cross-section at the open bottom end of the compartment. The oblique sidewalls facilitate the insertion of the tube in a compartment of the rack.

To provide flexibility of the compartment, a slot may be provided between the sidewalls of adjacent compartments. The open bottom end of the compartment may alternatively or in combination be provided with flexible lamellas to interact, e.g. in flexible cooperation, with a tube of the present invention.

The rack may further comprise a code for identification of the rack. The code is preferably an optically readable code, such as for example a bar code or a Data Matrix 2D-code. Alternatively or additionally, the rack may comprise an RFID-chip or tag.

Further the rack may comprise a lid. The lid may be adapted to interact with the rack, such that unintentional removal of the lid from the rack is substantially prevented.

The lid may be part of the packaging for the rack with tubes. The packaging may comprise a transparent foil covering the bottom of the rack, such that an ID code on tubes in the rack and/or on the rack itself may be read prior to unpacking the rack.

Preferably, the rack is made of ABS (acrylonitrile butadiene styrene), but other suitable materials, such as polycarbonate, polyethylene or polypropylene are also usable.

Preferably, the lid is made of a transparent or translucent material, such that an ID code on the rack may be read prior to unpacking the rack. The lid may be made of a polymer, such as polyethylene, polystyrene, or polypropylene, or other suitable materials.

The rack and lid are designed for provision of easy stacking of the rack, the lid or a combination of the rack and the lid. This facilitates automatic and manual handling and storing of a plurality of racks and lids.

In summary the tube, cap and rack of the present invention provide a safe handling of test samples of any kind.

It is an important advantage of the present invention that the rack may be turned upside down with tubes maintained in their respective compartments.

Another important advantage of the invention is that all handling of the present invention, e.g. placing tube in rack, capping and de-capping of tubes in rack, analyzing the content of tubes, moving a tube from rack, identifying tube and its contents, can be performed automatically by an automatic handling system.

Alternatively part or parts of the handling may be performed manually.

It is a further advantage of the present invention that the tube, the cap and the rack take up as little space as possible while providing the above-mentioned features.

The closed bottom end of the tube may bulge, but preferably, it is substantially flat so that the tube may be positioned on its bottom end in an upright position on a flat surface, such as a table.

Furthermore, a flat closed bottom end of the tube facilitates possible application of an optically readable identification code on the bottom end. A substantially flat surface ensures that the risk of errors during an automated optical reading of a coding is minimized by avoiding optical deformations.

BRIEF DESCRIPTION OF THE DRAWINGS

The invention will be described in further detail below with reference to the enclosed drawings, wherein

FIGS. 13A-D illustrate an embodiment of a tool for capping and de-capping a tube according to the invention.

DETAILED DESCRIPTION OF THE INVENTION

Figure 1:
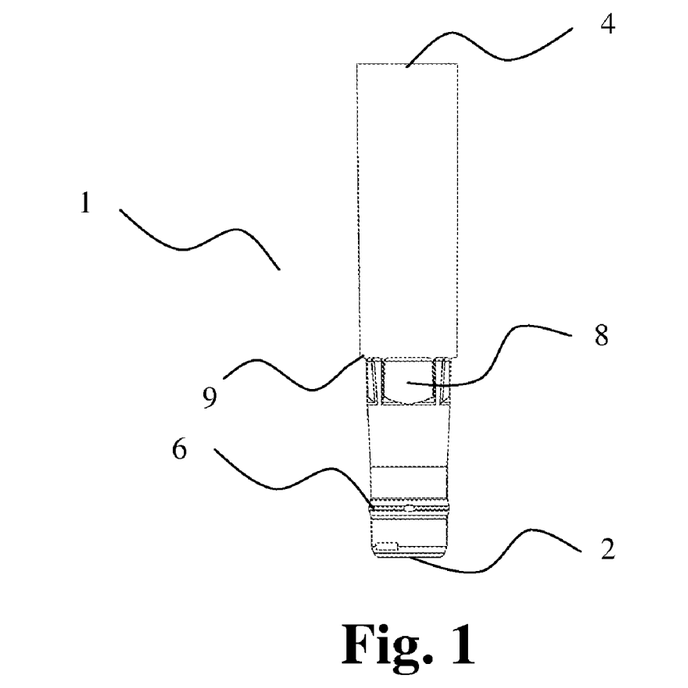
FIG. 1 is a side view of a preferred embodiment of the tube.

FIG. 1 shows a preferred embodiment of the tube of the present invention. The tube 1 has a closed bottom end 2 and an open top end 4. The outer surface of the closed bottom end 2 is colored in black to provide for the application of an identification code. The coloring is incorporated in the tube during the manufacturing process. A bead 6 is provided on a flexible part of the tube, i.e. above the solid closed bottom end 2. The bead cooperates with the sides of the rack compartments in a flexible manner to prevent the tubes from being unintentionally removed from the rack. An outer part 8 of the tube seen from a cross-sectional view in a plane perpendicular to the longitudinal extension of the tube is in this embodiment substantially shaped as a square. The part 8 prevents in cooperation with the compartments of the rack in at least one position of the tube in a compartment of the rack the tube from rotating. An edge 9 prevents the tube from dropping further in the rack when the part 8 is fitted in the compartment.

Figure 2A:
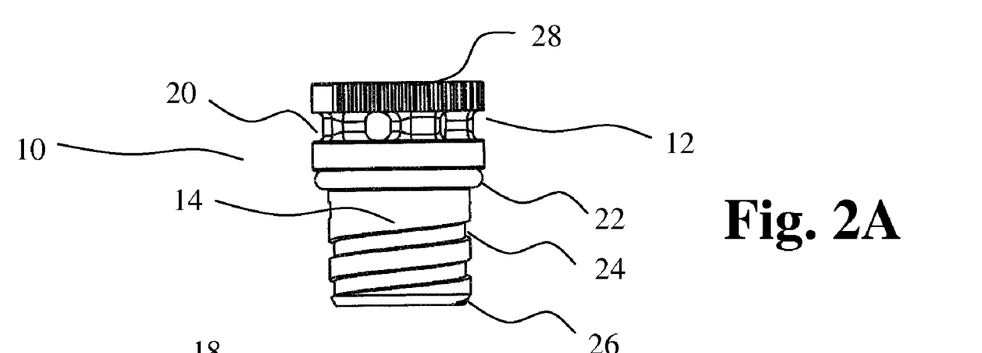
FIG. 2A is a side view of the cap of the present invention.
Figure 2B:
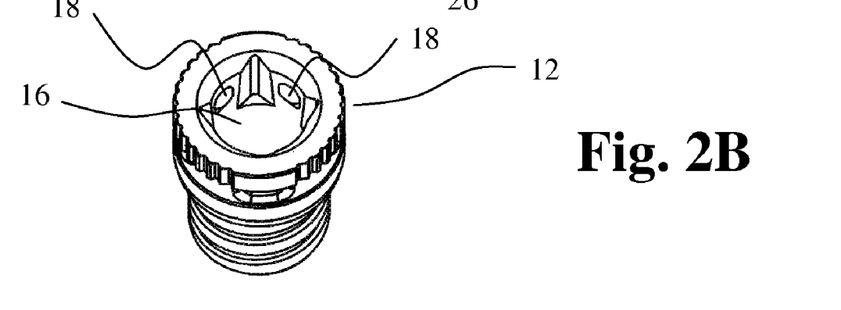
FIG. 2B is a perspective view from above of the cap of the present invention.

FIGS. 2A and 2B show a side view and a perspective view from above of an embodiment of the cap of the present invention. FIG. 2A shows the cap 10 with the head part 12 and the plug part 14. FIG. 2B is a top view of the cap and shows the head part 12 having a substantially squared depression 16 for interaction with a tool for capping or de-capping the tube. The depression may further be used for interaction with a tool for grabbing and moving the tube with the cap. The depression 16 has four holes 18, one in each side of the substantially square depression for removable interaction with a tool. The cap is provided with an annular recess 20 on the outer surface of the head part for engagement with a tool. Further, the cap 10 comprises a gasket 22 for sealing the tube. The embodiment of the cap shown in FIGS. 2A and 2B further comprises a threading 24 on the plug part 14 of the cap, the end of the plug part 26 being tapered for easy engagement of the cap with the tube. The head part of the cap further comprises a plurality of longitudinal recesses 28 on the outer surface to facilitate manual capping and de-capping.

Figure 3A:
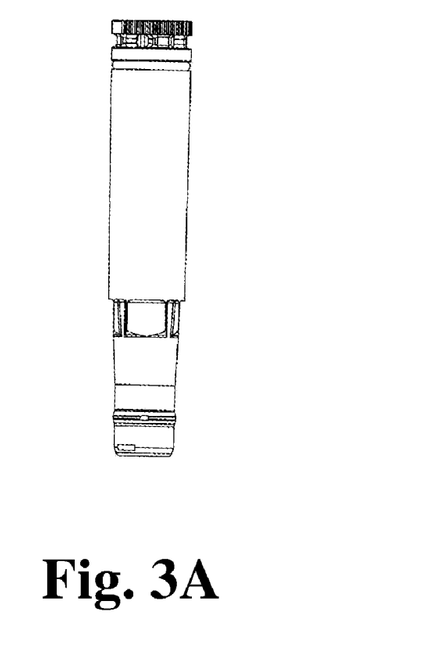
FIG. 3A is a side view of the tube with the cap.

FIG. 3A shows a side view of an embodiment of the tube with the cap. The tube according to the invention is especially intended for use in handling of samples with volume up to 1 ml, preferably 0.5 or 1 ml. During freezing, a test sample typically expands. To take into account this expansion and at the same time not take up more space than necessary the volume of the tube when the cap is put on is 5-20%, preferably 10% larger than the volume of the un-frozen sample. The preferred internal volume of the tube is thus 1.1 ml or 0.55 ml when the tube is capped.

Figure 3B:
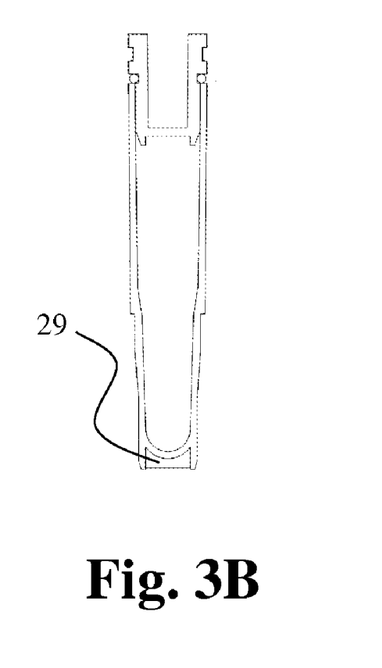
FIG. 3B is a cross section of an embodiment of the tube

FIG. 3B schematically shows a cross-section of an embodiment of the tube and cap. A part 29 may be colored to provide for application of an identification code. The part 29 may have an identification code and may be countersunk to prevent it from being scratched. The part 29 may be molded on the tube and then provided with an identification code, or an identification code may be applied to the part 29 prior to attachment of the part to the tube. The part 29 may also be an integrated part of the tube.

Figure 4:
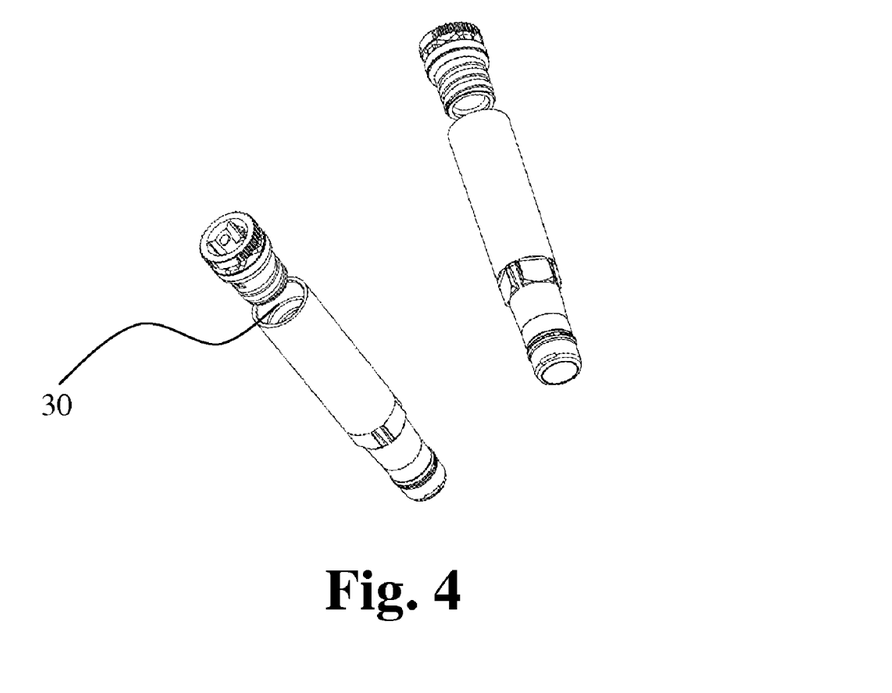
FIG. 4 shows the tube and the cap in different positions.

FIG. 4 shows an embodiment of the tube and the cap in different positions. The tube 1 has at the open top end an internal threading 30 to facilitate rotational attachment of the cap to the tube.

Figure 5:
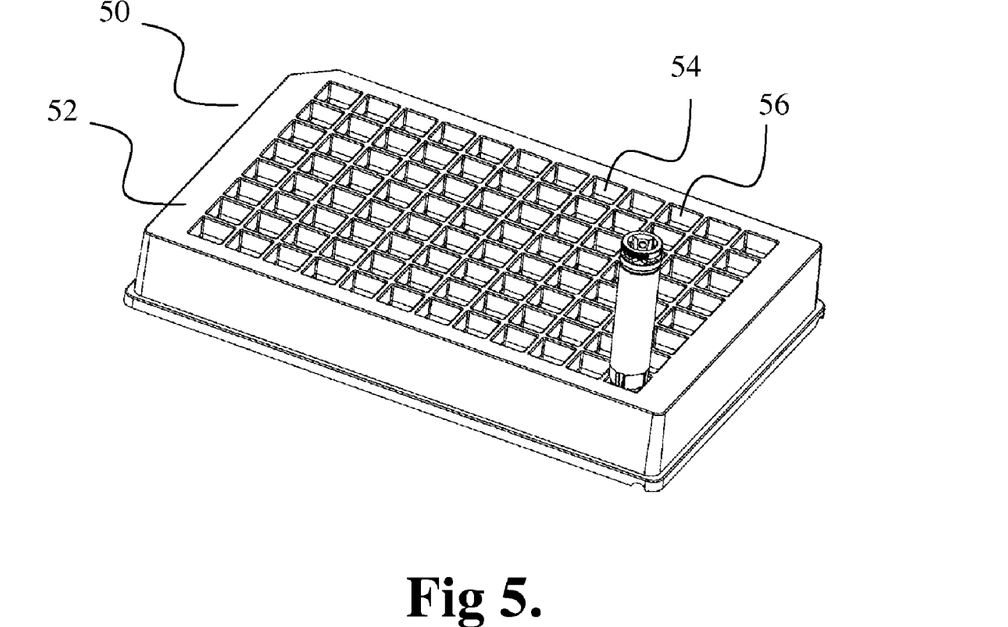
FIG. 5 shows the tube in one position in a compartment of the rack.
Figure 6:
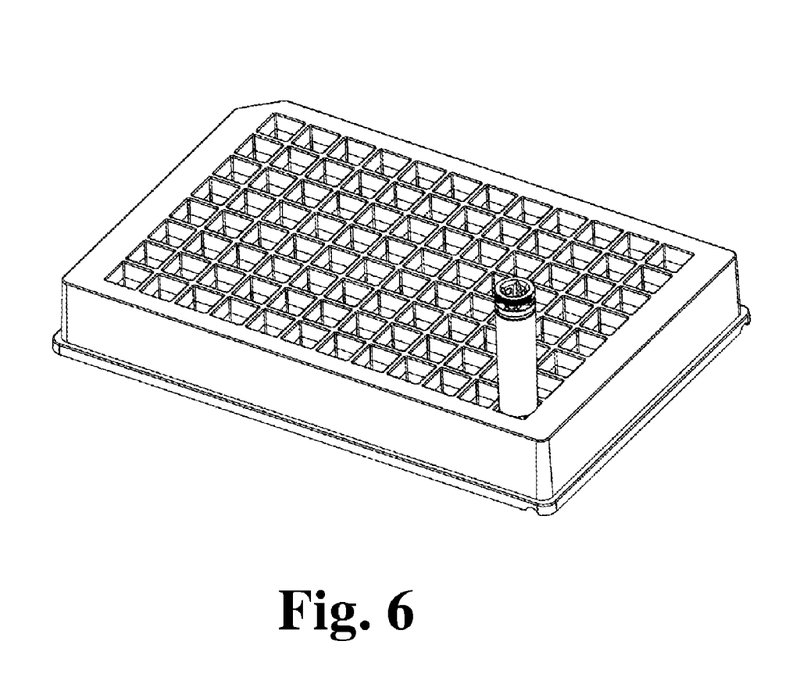
FIG. 6 shows the tube in another position in a compartment of the rack.

FIGS. 5 and 6 show an embodiment of the rack according to the invention accommodating a tube in two different positions. The rack 50 comprises a frame 52 with a plurality of compartments 54 for holding a plurality of tubes according to the present invention in one position in a compartment of the rack cf. FIG. 5 and in another position in a compartment of the rack cf. FIG. 6. In the position illustrated in FIG. 5, the tube can rotate substantially freely. The tube may be rotated into at least one position wherein the part 8 fits in the compartment, and gravitation or another force may cause the tube to enter into the position shown in FIG. 6. In the position shown in FIG. 6, the non-circular part 8 of the tube prevents, in cooperation with the compartment, the tube from rotating. The edge 9 on the tube rests on the open top 56 end of the compartment thereby preventing the tube from further insertion in the rack.

The open top end 56 of a compartment is adapted to facilitate insertion and capture of the tube 1 in the compartment. No force has to be applied in the beginning of insertion. At some point during insertion of the tube 1 in a compartment of the rack, the bead 6 has to be forced inside the compartment, whereby the tube 1 and/or the compartment sidewalls are slightly deformed creating a slight resistance against the insertion. When the bead 6 reach the open bottom end (58 on FIG. 7A) of the compartment, the tube with the bead and/or the compartment are allowed to return to its original shape so that the width of the tube at the bead becomes slightly larger than the corresponding width of the compartment so that removal of the tube cannot be performed without application of a force to deform the tube with bead and/or the compartment sufficiently to allow the bead to re-enter the compartment. Also, the protrusions prevent the tubes from falling out of the compartments if the rack is turned upside down. In both positions shown in FIG. 5 and FIG. 6, the bead is positioned below the open bottom end of the compartment, which means that movement of the tube between the two positions shown in FIGS. 5 and 6 is not influenced by the bead.

Figure 7A:
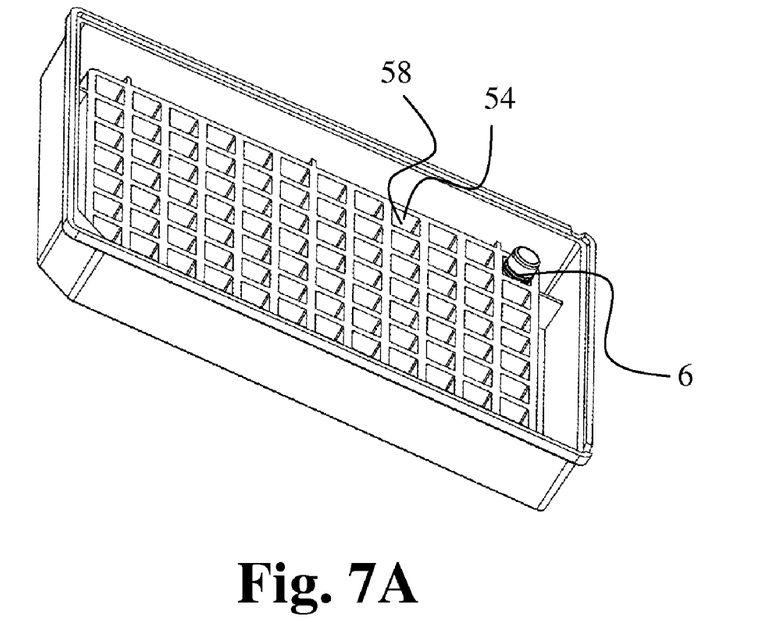
FIG. 7A shows the bottom of a rack with a tube accommodated in one position.

FIG. 7A shows the rack of FIG. 5 from another point of view. The rack has a plurality of compartments 54 having an open bottom end 58, the rack accommodating a tube according to the invention in the same position as in FIG. 5. The bead 6 has passed the sidewalls of the compartment and thereby prevents the tube from being unintentionally removed from the rack, e.g. falling out of the rack when rack is turned upside down.

Just above the bead 6, an outer circumference of a cross-section in the plane perpendicular to the longitudinal extension of the tube is substantially circular. Because of the circular circumference the tube can be inserted in a compartment of the rack without being rotationally fitted. Further, the tube may rotate substantially freely.

Figure 7B:
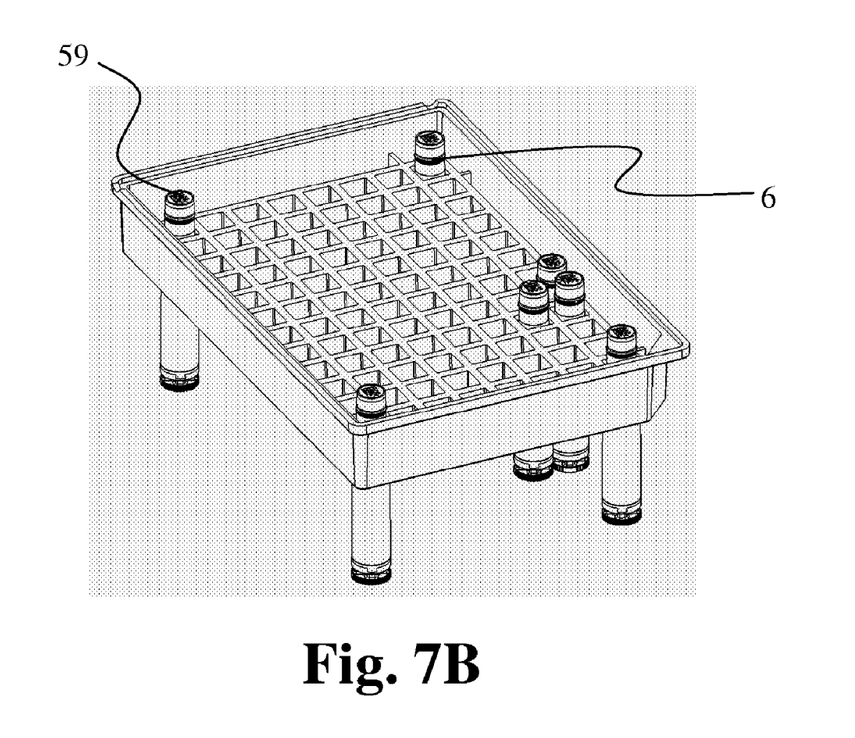
FIG. 7B shows the bottom of a rack with tubes accommodated in another position.

FIG. 7B shows a plurality of tubes accommodated in a rack seen from below. The position of each tube in the rack corresponds to the position of the tube in FIG. 6. When turning the rack upside down, gravity causes the tubes to move into the position which is shown for one tube in FIG. 7A. The bead 6 will prevent the tubes from falling out of the rack. The tubes are provided with an ID-code 59 at the bottom.

Figure 8:
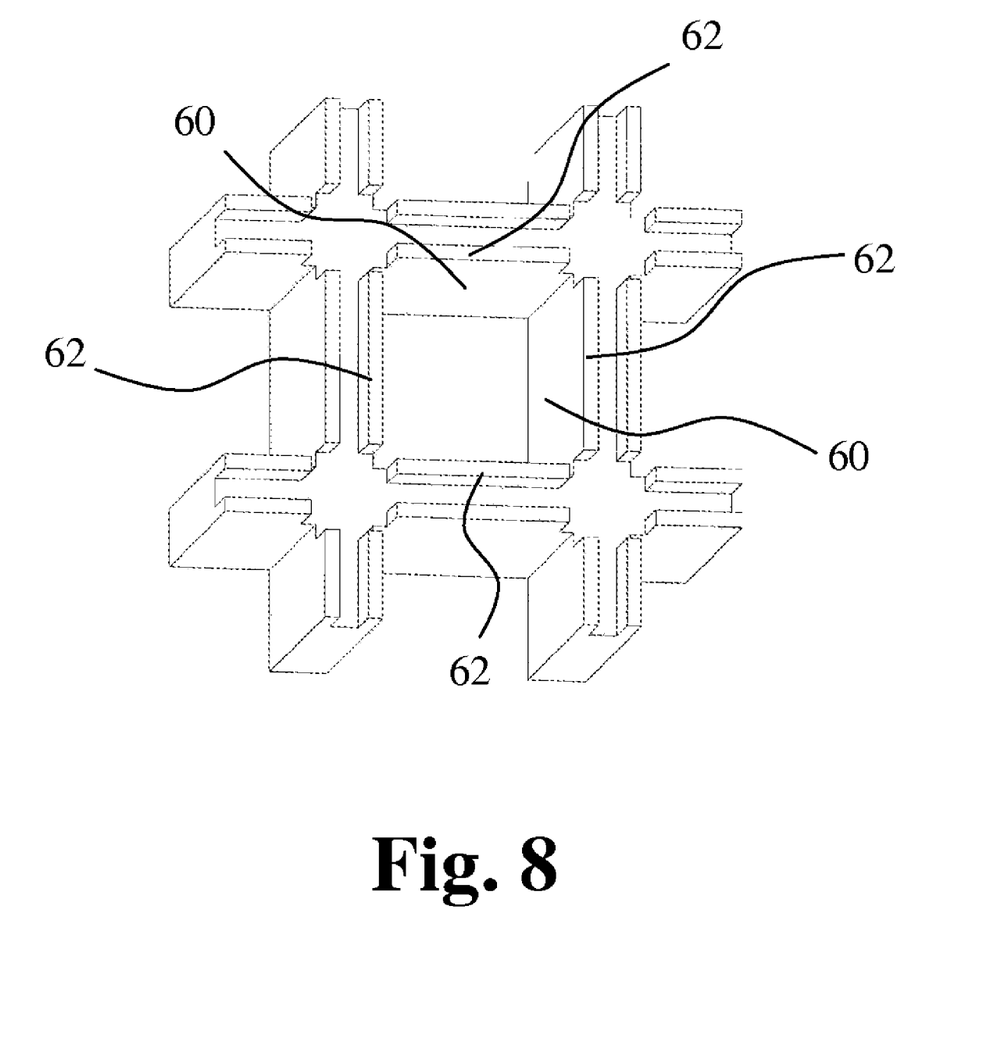
FIG. 8 shows a section of an embodiment of a rack of the present invention.

FIG. 8 illustrates from below a section of an embodiment of a rack of the present invention. In this embodiment the sidewalls 60 are at the open bottom end of the compartment provided with flexible lamellas 62 to interact in flexible cooperation with the tube. Alternatively only some of the four sidewalls of a compartment may be provided with lamellas. The lamellas may be divided into two or more parts.

Figure 9A:
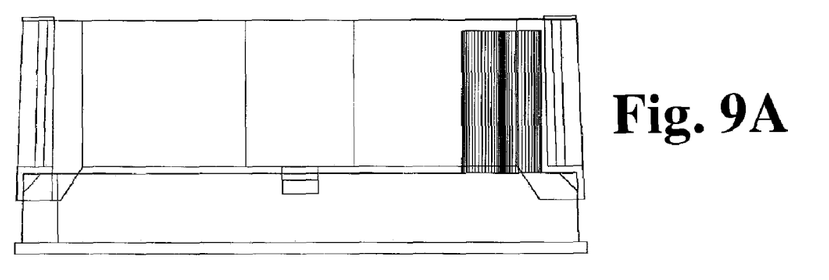
FIG. 9A is a side view of the lid and rack.
Figure 9B:
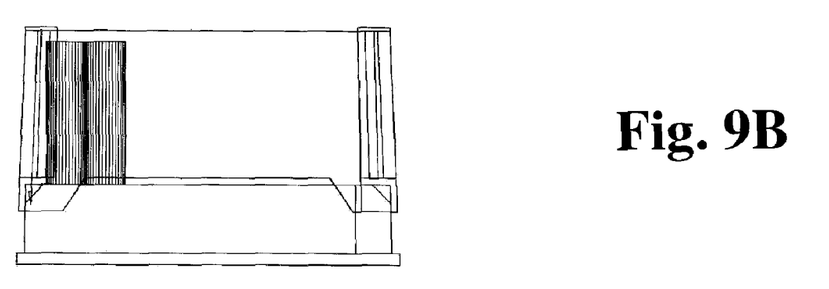
FIG. 9B is an end view of the lid and rack.

FIG. 9A is a side view, and FIG. 9B is an end view of an embodiment of the lid and rack. The lid has a member 70 at each side to, in cooperation with a slot 72 at each side of the rack, prevent unintentional removal of the lid from the rack.

Figure 10A:
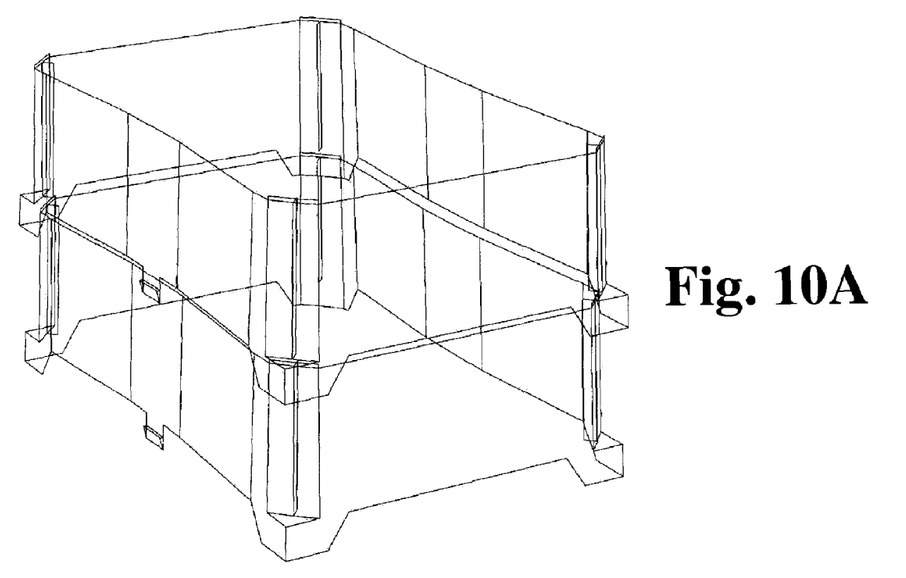
FIGS. 10A-C illustrate stacking of lids, racks and a combination of the two.
Figure 10B:
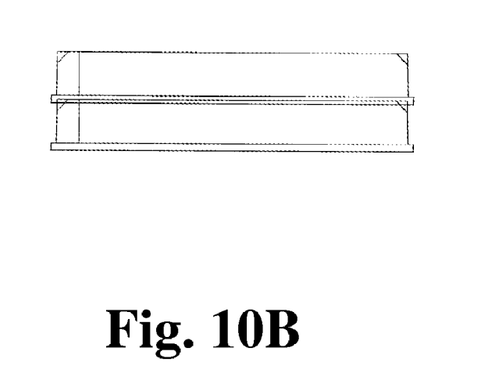
Figure 10C:
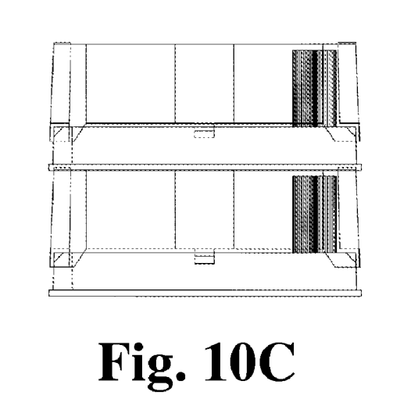

FIG. 10A illustrates the stacking of lids, FIG. 10B the stacking of racks, and FIG. 10C shows the stacking of racks with lids according to the invention.

Figure 11:
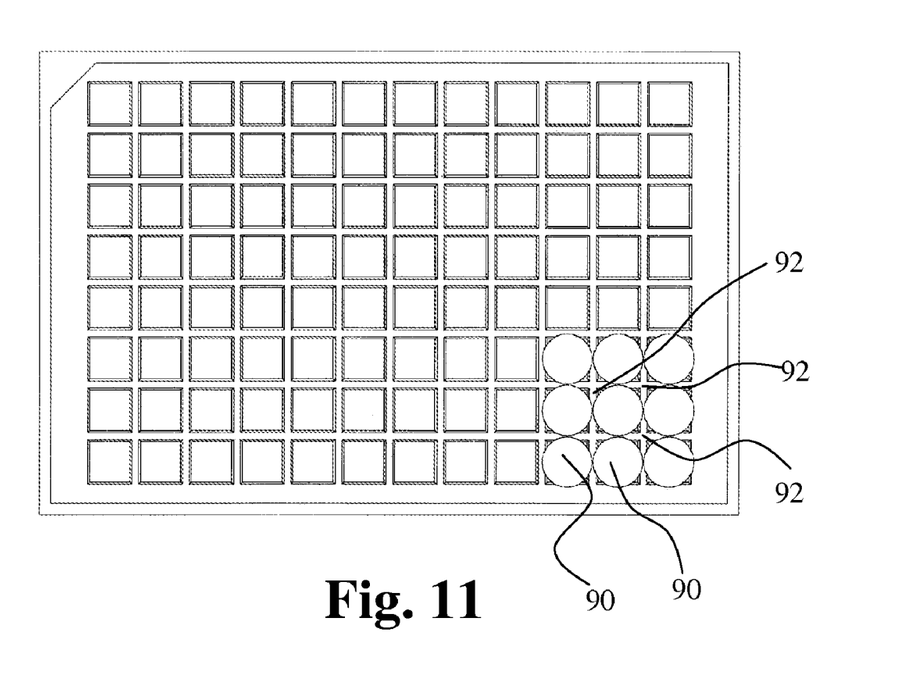
FIG. 11 is a top view of the rack accommodating 9 tubes according to the present invention.

FIG. 11 is a schematic top view of an embodiment of the rack accommodating 9 tubes with caps 90 according to the present invention. The interspaces 92 between the tubes may be used for a tool for moving the tube from or placing the tube in a compartment of the rack. The tool for moving the tube may in another embodiment engage with the depression 16 in the cap.

Figure 12A:
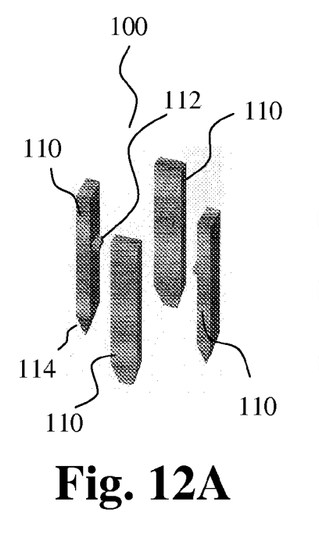
FIG. 12A illustrates a part of a tool for grabbing and moving a tube according to the present invention, and FIGS. 12B and 13C schematically illustrate the principle of grabbing the tube with a tool while positioned in a rack.

FIG. 12A illustrates a part 100 of an embodiment of a tool for grabbing and moving a tube according to the present invention. The tool comprises four arms 110, each arm having a protrusion 112 for engagement with a recess 20 on the head part of a cap. The end 114 of an arm 110 is tapered to facilitate insertion of the tool in the interspaces between the tubes with caps as illustrated in FIG. 13C. The length of the arm from the protrusion 112 to the end 114 of the arm is between 1-25 mm, preferably between 5-15 mm, to provide a firm grip on the tube.

Figure 12B:
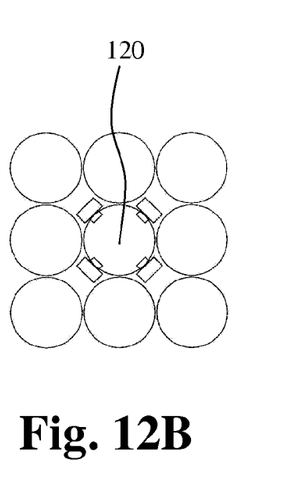
Figure 12C:
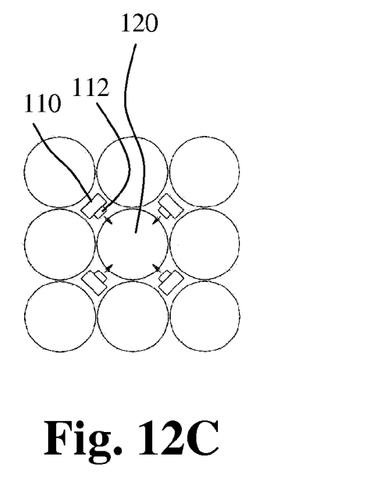

FIGS. 12B and 12C schematically illustrate the principle of operation of an embodiment of the tool for grabbing and inserting or removing the tube with the cap 120. The Figs. illustrate nine tubes with interspaces 92 positioned in a rack as shown in FIG. 11. In FIG. 12C the four arms 110 of the tool part 100 are positioned in the four interspaces 92 between the nine tubes, the protrusions 112 being on a level with the recess

20 on the head part of the cap. In FIG. 12B the tool has grabbed the tube with the cap by moving the arms 110 towards the center of the tube 120, whereby the protrusions 112 engage with the recess 20 in the head part of the cap. The tube with cap can now be moved from the rack with the tool while the rack is kept in a fixed position.

Figure 13A:
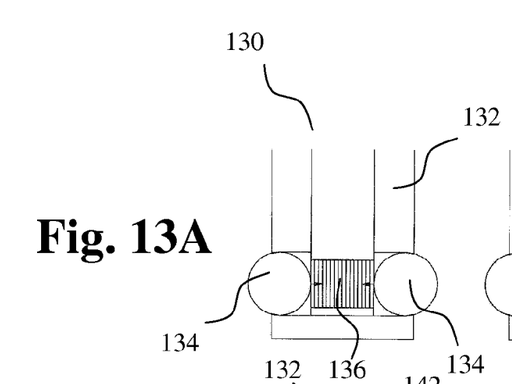
Figure 13B:
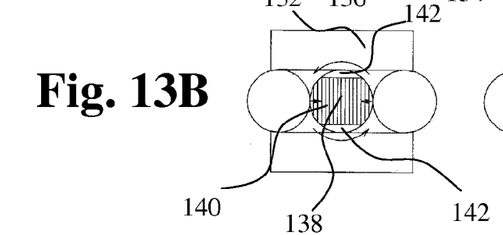
Figure 13C:
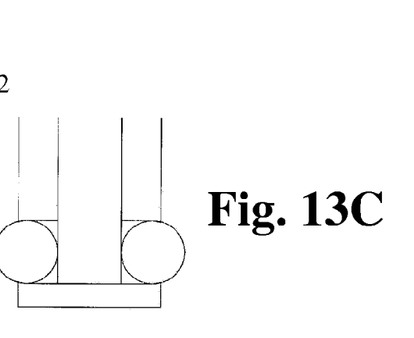
Figure 13D:
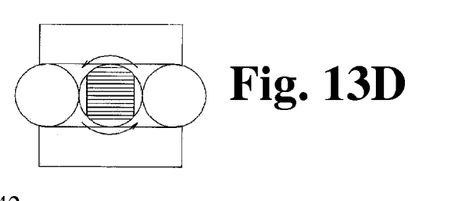

An embodiment of a tool 130 for capping and de-capping the tube is schematically illustrated in FIGS. 13A-D. A longitudinal section is shown on FIGS. 13A and 13C, and a cross section of an embodiment of the tool for capping and de-capping is shown in FIGS. 13B and 13D. The tool employs a ball catch principle. The tool comprises a substantially squared male part 132 for insertion into the depression of the head part of the cap. Two small balls 134 are positioned in the male part separated by a flexible member 136. In an alternative embodiment a rotatable cylinder 138 having a flexible part 140 and a solid part 142 may be provided as illustrated in FIGS. 13B and 13D for keeping the two balls in a flexible (FIG. 12B) and a fixed (FIG. 13D) state. In this way the tool for capping and de-capping the tube may also, in the locked state shown in FIG. 13D, be used for grabbing and inserting or removing the tube with the cap.

The invention claimed is:

1. A tube extending along a longitudinal axis comprising a container having a closed bottom end, an open top end, and a part that is adapted for flexible cooperation with a compartment of a rack for accommodation of the tube in such a way that in a first longitudinal position in the compartment, the tube is substantially free to rotate about the longitudinal axis of the tube in the compartment so that unintentional removal of the tube from the respective compartment is substantially prevented, and wherein the part adapted for flexible cooperation with a compartment of a rack comprises at least one of a protrusion positioned at a hollow part on the outside of the tube and a bead substantially covering the circumference of the tube wherein an outer circumference of a cross-section in a plane perpendicular to the longitudinal extension of the tube is non-circular for definition of at least one angular position of the tube so that when moving the tube into a second longitudinal position in the compartment, the tube can not be rotated in said second longitudinal position, and wherein the outer circumference comprises at least one protrusion for definition of at least one position of the tube in a compartment in which position the tube can not be rotated.

2. A tube according to claim 1, wherein the bead covers the entire circumference of the tube.

3. A tube according to claim 1, wherein the bead is divided into sections.

4. A tube according to claim 1, wherein the bead is positioned at a hollow part of the tube.

5. A tube according to claim 4, wherein the cross-section is substantially polygonal.

6. A tube according to claim 1, wherein the cross-section is substantially polygonal.

7. A tube extending along a longitudinal axis comprising a container and having a closed bottom end, an open top end, and a part that is adapted for insertion into a compartment of a rack and for flexible cooperation with the compartment in such a way that unintentional removal of the tube from the compartment is substantially prevented in a first longitudinal position in the compartment and wherein an outer circumference of a cross-section in a plane perpendicular to the longitudinal extension of the tube is non-circular for definition of at least one angular position of the tube for moving the tube into a second longitudinal position in the compartment in which second longitudinal position the tube can not be rotated.

8. A tube according to claim 7, wherein the part of the tube adapted for flexible cooperation with a compartment of the rack, comprises at least one protrusion on the outside of the tube.

9. A tube according to claim 8, wherein the at least one protrusion is positioned at a hollow part of the tube.

10. A tube according to claim 8, wherein the protrusion comprises a bead.

11. A tube according to claim 7, wherein the outer circumference comprises at least one protrusion for definition of at least one position of the tube in a compartment in which position the tube can not be rotated.

12. A tube according to claim 7, wherein the cross-section is substantially polygonal.

13. A tube according to claim 7, wherein the tube is made of a polymer.

14. A tube according to claim 7, further comprising a threading on the inside of the tube for engagement with a threaded cap.

15. A tube according to claim 7, further comprising an ID-code at the closed bottom end of the tube for identification of the tube and its contents.

16. A tube according to claim 7, the tube having a cap.

17. A tube and a cap according to claim 16, wherein the cap has a plug part and a head part, the head part having a substantially polygonal part adapted for interaction with a tool for capping or de-capping the tube.

18. A tube and a cap according to claim 17, wherein the head part of the cap has a substantially polygonal protrusion for interaction with a tool for capping or de-capping the tube.

19. A tube and a cap according to claim 17, wherein the head part of the cap has a substantially polygonal depression for interaction with a tool for capping or de-capping the tube.

20. A tube and a cap according to claim 19, wherein the depression has at least one recess in a side thereof for removable attachment of the cap to the tool.

21. A tube and a cap according to claim 19, wherein the depression has at least one hole in a side thereof for removable attachment of the cap to the tool.

22. A tube and a cap according to claim 17, wherein the cap further comprises at least one recess on the outside surface of the head part for engagement with a tool for positioning of the tube with the cap in the rack.

23. A tube and a cap according to claim 16, wherein the cap further comprises a gasket for sealing the tube when the cap is positioned in the tube.

24. A tube and a cap according to claim 23, wherein the gasket is an O-ring.

25. A tube and a cap according to claim 23, wherein the gasket is molded onto the cap during manufacturing.

26. A tube and a cap according to claim 17, wherein the cap further comprises a threading on the plug part.

27. A tube and a cap according to claim 17, wherein the end of the plug part is tapered for easy engagement with the tube.

28. A tube according to claim 1 and a rack comprising a frame with a plurality of non-circular compartments for holding a plurality of tubes.

29. A tube and a cap according to claim 16 and a rack comprising a frame with a plurality of compartments for holding a plurality of tubes.

30. A tube and a rack according to claim 28, wherein the rack complies with at least some of the dimensions of the SBS-standard.

31. A tube and a rack according to claim 28, further comprising a lid so that racks with lids can be stacked.

32. A tube according to claim 1, further comprising a polymer cap having a plug part and a head part, the head part having a substantially polygonal part adapted for interaction with a tool for capping or de-capping the tube and wherein the polygonal part has at least one recess in a side thereof for removable attachment of the cap to the tool.

33. A cap according to claim 32, wherein the substantially polygonal part is a depression for interaction with a tool for capping or de-capping the tube.

34. A cap according to claim 32, wherein the substantially polygonal part is a protrusion for interaction with a tool for capping or de-capping the tube.

35. A cap according to claim 32, wherein the at least one recess comprises a hole.

36. A cap according to claim 32, wherein the cap further comprises at least one recess on the outside surface of the head part for engagement with a tool for positioning of the tube in the rack.

37. A tube according to claim 7, further comprising a polymer cap having a plug part and a head part, the head part having a substantially polygonal part adapted for interaction with a tool for capping or de-capping the tube and wherein the cap further comprises at least one recess on the outside surface of the head part for interaction with a tool for moving the tube with the cap.

38. A cap according to claim 37, wherein the substantially polygonal part is a depression for interaction with a tool for capping or de-capping the tube.

39. A cap according to claim 37, wherein the substantially polygonal part is a protrusion for interaction with a tool for capping or de-capping the tube.

40. A cap according to claim 37, wherein the at least one recess comprises a hole.

41. A cap according to claim 37, wherein the polygonal part has at least one recess in a side thereof for removable attachment of the cap to the tool.

42. A cap according to claim 32, wherein the cap further comprises a gasket for sealing the tube when the cap is positioned in the tube.

43. A cap according to claim 42, wherein the gasket is an O-ring.

44. A cap according to claim 42, wherein the gasket is molded onto the cap during manufacturing.

45. A cap according to claim 32, wherein the cap further comprises a threading on the plug part for engagement with a threaded tube.

46. A cap according to claim 32, wherein the plug part is tapered for easy engagement with the tube.

* * * * *